(12) United States Patent
Song et al.

(10) Patent No.: US 10,501,583 B2
(45) Date of Patent: Dec. 10, 2019

(54) METHOD FOR PREPARING POLYHEDRAL OLIGOMERIC SILSESQUIOXANE

(71) Applicant: LG Chem, Ltd., Seoul (KR)

(72) Inventors: Young Jee Song, Daejeon (KR); Ji Young Choi, Daejeon (KR); Min Hyung Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/743,830

(22) PCT Filed: Jan. 26, 2017

(86) PCT No.: PCT/KR2017/000992
§ 371 (c)(1),
(2) Date: Jan. 11, 2018

(87) PCT Pub. No.: WO2017/131489
PCT Pub. Date: Aug. 3, 2017

(65) Prior Publication Data
US 2018/0201734 A1    Jul. 19, 2018

(30) Foreign Application Priority Data
Jan. 28, 2016 (KR) .................. 10-2016-0010910

(51) Int. Cl.
| C08G 77/20 | (2006.01) |
| C07F 7/21 | (2006.01) |
| C08G 77/16 | (2006.01) |
| C08G 77/24 | (2006.01) |
| C08G 77/00 | (2006.01) |

(52) U.S. Cl.
CPC .............. *C08G 77/20* (2013.01); *C07F 7/21* (2013.01); *C08G 77/16* (2013.01); *C08G 77/24* (2013.01); *C08G 77/70* (2013.01)

(58) Field of Classification Search
None
See application file for complete search history.

(56) References Cited

U.S. PATENT DOCUMENTS

| 5,484,867 A | 1/1996 | Lichtenhan et al. |
| 5,853,808 A | 12/1998 | Arkles et al. |
| 6,329,490 B1 * | 12/2001 | Yamashita ........... C08G 77/045 528/12 |
| 7,235,619 B2 | 6/2007 | Morimoto et al. |
| 7,485,692 B2 | 2/2009 | Schwab et al. |
| 8,506,853 B2 | 8/2013 | Wada et al. |
| 2003/0055193 A1 | 3/2003 | Lichtenhan et al. |
| 2004/0030084 A1 | 2/2004 | Morimoto et al. |
| 2005/0010012 A1 | 1/2005 | Jost et al. |
| 2010/0310780 A1 | 12/2010 | Martin et al. |
| 2011/0160330 A1 | 6/2011 | Nagai et al. |
| 2013/0165617 A1 | 6/2013 | Hwang et al. |

FOREIGN PATENT DOCUMENTS

| CN | 103183702 A | 7/2013 | |
| JP | H111512474 A | 10/1999 | |
| JP | 2000290286 A | 10/2000 | |
| JP | 2002265607 A | 9/2002 | |
| JP | 2004143449 A | 5/2004 | |
| JP | 2005509042 A | 4/2005 | |
| JP | 2006096735 A | 4/2006 | |
| JP | 2007015991 A | 1/2007 | |
| JP | 2009060007 A | 3/2009 | |
| JP | 2011098939 A | 5/2011 | |
| JP | 4742212 B2 | 8/2011 | |
| JP | 2012251035 A | 12/2012 | |
| JP | 5344869 B2 | 11/2013 | |
| KR | 20000063082 A | 10/2000 | |
| KR | 100722731 B1 | 5/2007 | |
| KR | 101137755 B1 | 7/2012 | |
| KR | 101248530 B1 | 4/2013 | |
| KR | 20140021634 A | 2/2014 | |
| KR | 20140141115 A | 12/2014 | |
| WO | WO-0110871 A1 * | 2/2001 | ............ C07F 7/0874 |
| WO | 2010024119 A1 | 3/2010 | |
| WO | 2010067685 A1 | 6/2010 | |

OTHER PUBLICATIONS

International Search Report for Application No. PCT/KR2017/000992 dated May 19, 2017.
Tanaka et al., "Synthesis of Fluorinated Organic-Inorganic Hybrid Polymer and Its Application for Surface Modification of Polmeric Materials," Journal of Network Polymer, Japan, vol. 33, No. 1, Jan. 10, 2012, pp. 16-25.
Chujo et al., "POSS-Based Functional Materials," Journal of Network Polymer, Japan, vol. 32, No. 5, Sep. 10, 2011, pp. 233-244.
Oikawa et al., "Surface Property Control of Epoxy Hybrid Film Composed of Fluorinated Polyhedral Oligomeric Silsesquioxane-Terminated Polymers," Journal of Network Polymer, Japan, vol. 33, No. 4, Jul. 10, 2012, pp. 193-203.

* cited by examiner

*Primary Examiner* — Clinton A Brooks
*Assistant Examiner* — Kofi Adzamli
(74) *Attorney, Agent, or Firm* — Lerner, David, Littenberg, Krumholz & Mentlik, LLP

(57) ABSTRACT

The present invention relates to a method for preparing a polyhedral oligomer silsesquioxane. The preparation method includes the step of reacting a reaction mixture containing at least two types of silane compounds and a tetraalkylammonium hydroxide having 2 to 5 carbon atoms at a temperature of 5° C. or below.

12 Claims, No Drawings

METHOD FOR PREPARING POLYHEDRAL OLIGOMERIC SILSESQUIOXANE

CROSS-REFERENCE TO RELATED APPLICATION(S)

The present application is a national phase entry under 35 U.S.C. § 371 of International Application No. PCT/KR2017/000992 filed on Jan. 26, 2017, which claims priority from Korean Patent Application No. 10-2016-0010910 filed on Jan. 28, 2016 with the Korean Intellectual Property Office, the disclosures of which are incorporated herein by reference.

TECHNICAL FIELD

The present relates to a method for preparing a polyhedral oligomeric silsesquioxane.

BACKGROUND ART

A siloxane structure consisting of a Si—O—Si linkage is generally defined by distinguishing it into 4 types (Q, T, D, and M).

Among them, polysiloxanes represented as $[RSiO_{1.5}]_y$ have the T unit structure among the 4 types of structures, and the scientific name thereof is polysilsesquioxane.

Polysilsesquioxanes are synthesized by using a hydrolysis-polymerization method, and in particular, a method using trialkoxysilane and a hydrolysis-polymerization method using trichlorosilane have been widely known up until now.

The structure of thus-synthesized polysilsesquioxanes is generally known to have high regularity.

However, as the instrumental analysis techniques in the field of chemistry have been significantly improved, it has been determined that polysilsesquioxanes have a cage structure, such as 6, 8, 10, and 12 dimers, a ladder-type, or an irregular structure.

It is believed that the mechanical/physical properties thereof do not reach what was expected from the design of polymer structures due to the mixture of these structures.

DISCLOSURE

Technical Problem

It is one object of the present invention to provide a preparation method capable of providing a polyhedral oligomeric silsesquioxane having a cage structure with high purity and a high yield.

Technical Solution

According to one embodiment of the present invention, there is provided a method for preparing a polyhedral oligomeric silsesquioxane including the step of: reacting a reaction mixture containing a first silane compound represented by Chemical Formula 1 below, a second silane compound represented by Chemical Formula 2 below, and tetraalkylammonium hydroxide having 2 to 5 carbon atoms at a temperature of 5° C. or below.

  [Chemical Formula 1]

  [Chemical Formula 2]

In Chemical Formulae 1 and 2, A is a single bond, an alkylene group having 1 to 10 carbon atoms, an arylene group having 6 to 30 carbon atoms, —O—Si($R^3$)($R^4$)—, -or —O—Si($R^3$)($R^4$)—$R^5$—, $R^1$ is a monovalent moiety derived from a hydrocarbon having 1 to 30 carbon atoms substituted with a halogen, $R^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —$NH_2$, —NH—$R^6$, —$NH_3X^3$, —COON, —$CONH_2$, —CN, —SH, a glycidyl group, a glycidyloxy group, and maleimide, $X^1$ and $X^2$ are each independently an alkoxy group having 1 to 5 carbon atoms, Cl, Br, or I, $R^3$ and $R^4$ are each independently an alkyl group having 1 to 5 carbon atoms, $R^5$ is an alkylene group having 1 to 12 carbon atoms, $R^6$ is an alkyl group having 1 to 10 carbon atoms, an aryl group having 6 to 30 carbon atoms, or an alkyl group having 1 to 10 carbon atoms substituted with an amino group, and $X^3$ is a halogen.

Specifically, as the first silane compound, a compound in which $R^1$ may be trifluoromethyl, trifluoroethyl, trifluoropropyl, trifluorobutyl, pentafluorobutyl, trifluoropentyl, pentafluoropentyl, heptafluoropentyl, trifluorohexyl, pentafluorohexyl, heptafluorohexyl, nonafluorohexyl, trifluoroheptyl, pentafluoroheptyl, heptafluoroheptyl, nonafluoroheptyl, dodecafluoroheptyl, chloropropyl, (chloromethyl)phenyl, (chloromethyl)phenylethyl, or dibromoethyl can be used.

More specifically, as the first silane compound, at least one selected from the group consisting of (trifluoropropyl)trimethoxysilane, (trifluorobutyl)trimethoxysilane, (pentafluorobutyl)trimethoxysilane, (trifluoropentyl)trimethoxysilane, (pentafluoropentyl)trimethoxysilane, (heptafluoropentyl)trimethoxysilane, (trifluorohexyl)trimethoxysilane, (pentafluorohexyl)trimethoxysilane, (heptafluorohexyl)trimethoxysilane, (nonafluorohexyl)trimethoxysilane, (trifluoroheptyl)trimethoxysilane, (pentafluoroheptyl)trimethoxysilane, (heptafluoroheptyl)trimethoxysilane, (nonafluoroheptyl)trimethoxysilane, (dodecafluoroheptyl)trimethoxysilane, (chloropropyl)trimethoxysilane, [(chloromethyl)phenyl]trimethoxysilane, [(chloromethyl)phenylethyl]trimethoxysilane, (dibromoethyl)trimethoxysilane, and the like may be used.

Meanwhile, as the second silane compound, a compound in which $R^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxycyclohexyl group, an epoxycycloheptoxy group, a vinyl group, an allyl group, and a norbornene group, or a monovalent moiety derived from a hydrocarbon substituted with at least one substituent selected from the group consisting of cyclohexanediol, trimethylolpropane, glycerol, 3-hydroxy-3-methylbutane, aminopropyl, aniline, N-methylaminopropane, N-phenylaminopropane, N-(aminoethyl)aminopropane, propylammonium chloride, propylnitrile, propylthiol, glycidyl oxypropane, N-propylmaleimide, and maleamic acid can be used.

Further, as the second silane compound, a compound in which A is a single bond, methylene, ethylene, propylene, phenylene, —O—Si(CH$_3$)(CH$_3$)—, or —O—Si(CH$_3$)(CH$_3$)—CH$_2$CH$_2$CH$_2$— can be used.

More specifically, as the second silane compound, at least one selected from the group consisting of (3-(meth)acryloxypropyl)trimethoxysilane, (2,3-dihydroxypropoxypropyl)trimethoxysilane, (3,4-dihydroxyhexylethyl)trimethoxysilane, (3-hydroxy-3-methylbutyldimethylsiloxy)trimethoxysilane 3,4-epoxyhexylpropyl)trimethoxysilane, (3,4-epoxyhexylethyldimethylsiloxy)trimethoxysilane, (3-aminopropyl)trimethoxysilane, (N-aminoethylaminopropyl)trimethoxysilane, (aminophenyl)trimethoxysilane, (N-phenylaminopropyl)trimethoxysilane, (N-methylaminopropyl)trimethoxysilane, (3-cyanopropyl)trimethoxysilane, (3-mercaptopropyl)trimethoxysilane, (3-glycidyloxypropyl)trimethoxysilane, vinyltrimethoxysilane, allyltrimethoxysilane, (trimethoxysilyl)norbornene, N-[3-(trimethoxysilyl)propyl]maleimide, N-[3-(trimethoxysilyl)propyl]maleamic acid, and the like may be used.

As the tetraalkylammonium hydroxide having 2 to 5 carbon atoms, tetrabutylammonium hydroxide may be used.

The tetraalkylammonium hydroxide having 2 to 5 carbon atoms may be used in an amount of 0.001 to 100 moles based on 100 moles of the entire silane compounds.

Meanwhile, in the preparation method of one embodiment, the reaction mixture may be reacted in the presence of an organic solvent.

Herein, an ether solvent may be used as the organic solvent.

In the preparation method of one embodiment, the reaction mixture may be reacted for 5 to 128 hours.

The polyhedral oligomeric silsesquioxane prepared according to the preparation method of one embodiment may be a compound represented by Chemical Formula 3 below.

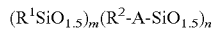   [Chemical Formula 3]

In Chemical Formula 3, A is a single bond, an alkylene group having 1 to 10 carbon atoms, an arylene group having 6 to 30 carbon atoms, —O—Si(R$^3$)(R$^4$)—, or —O—Si(R$^3$)(R$^4$)—R$^5$—, R$^1$ is a monovalent moiety derived from a hydrocarbon having 1 to 30 carbon atoms substituted with a halogen, R$^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —NH$_2$, —NH—R$^6$, —NH$_3$X$^3$, —COON, —CONH$_2$, —CN, —SH, a glycidyl group, a glycidyloxy group, and maleimide, R$^3$ and R$^4$ are each independently an alkyl group having 1 to 5 carbon atoms, R$^5$ is an alkylene group having 1 to 12 carbon atoms, R$^6$ is an alkyl group having 1 to 10 carbon atoms, an aryl group having 6 to 30 carbon atoms or an alkyl group having 1 to 10 carbon atoms substituted with an amino group, X$^3$ is a halogen, and m and n are each independently an integer of 1 to 13, with the proviso that the sum of m and n is an integer of 6 to 14.

Advantageous Effects

Through the method for preparing a polyhedral oligomeric silsesquioxane according to one embodiment of the present invention, it is possible to minimize the production of by-products of other structures and to synthesize high purity polyhedral oligomeric silsesquioxanes with a high yield.

DETAILED DESCRIPTION OF THE EMBODIMENTS

Hereinafter, the method for preparing a polyhedral oligomeric silsesquioxane according to specific embodiments, will be described.

According to one embodiment of the present invention, there is provided a method for preparing a polyhedral oligomeric silsesquioxane including the step of: reacting a reaction mixture containing a first silane compound represented by Chemical Formula 1 below, a second silane compound represented by Chemical Formula 2 below, and a tetraalkylammonium hydroxide having 2 to 5 carbon atoms at a temperature of 5° C. or below.

   [Chemical Formula 1]

   [Chemical Formula 2]

In Chemical Formulae 1 and 2, A is a single bond, an alkylene group having 1 to 10 carbon atoms, an arylene group having 6 to 30 carbon atoms, —O—Si(R$^3$)(R$^4$)—, or —O—Si(R$^3$)(R$^4$)—R$^5$—, R$^1$ is a monovalent moiety derived from a hydrocarbon having 1 to 30 carbon atoms substituted with a halogen, R$^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —NH$_2$, —NH—R$^6$, —NH$_3$X$^3$, —COON, —CONH$_2$, —CN, —SH, a glycidyl group, a glycidyloxy group, and maleimide, X$^1$ and X$^2$ are each independently an alkoxy group having 1 to 5 carbon atoms, Cl, Br, or I, R$^3$ and R$^4$ are each independently an alkyl group having 1 to 5 carbon atoms, R$^5$ is an alkylene group having 1 to 12 carbon atoms, R$^6$ is an alkyl group having 1 to 10 carbon atoms, an aryl group having 6 to 30 carbon atoms, or an alkyl group having 1 to 10 carbon atoms substituted with an amino group, and X$^3$ is a halogen.

As used herein, the hydrocarbon is a compound consisting of carbon and hydrogen, and refers to including all unsaturated hydrocarbons and saturated hydrocarbons containing carbon-carbon double bonds and/or carbon-carbon triple bonds.

The hydrocarbon may be linear, branched, or cyclic, or may include at least two structures thereof.

More specifically, the hydrocarbon may be an alkane, an alkene, an alkyne, or an arene containing linear, branched, or cyclic structures, one or more of which may be substituted by another.

Further, as used herein, the monovalent moiety derived from a hydrocarbon or the monovalent moiety derived from a substituted hydrocarbon refers to a monovalent radical in which one hydrogen radical is removed from the hydrocarbon or the substituted hydrocarbon.

Polysilsesquioxanes may have various structures, such as random, ladder type, cage, partial cage, etc., and among them, polysilsesquioxanes having a cage structure are referred to as polyhedral oligomeric silsesquioxanes.

These polyhedral oligomeric silsesquioxanes can easily introduce a plurality of functional groups and effectively express the properties of functional groups, while taking the silsesquioxane backbone as a core, and thus they are gaining much attention in various technical fields.

However, a method known for synthesizing polyhedral oligomeric silsesquioxanes has a problem that polysilsesquioxanes having random or ladder-type structures are produced, in addition to the polyhedral oligomeric silsesquioxanes.

Accordingly, the present inventors conducted an extensive study on a method for synthesizing polyhedral oligomeric silsesquioxanes and discovered a method for obtaining polyhedral oligomeric silsesquioxanes with high purity and a high yield while minimizing the production of by-products having a high molecular weight, thereby completing the present invention.

Specifically, according to the preparation method of one embodiment, by reacting a reaction mixture containing a first silane compound represented by Chemical Formula 1, a second silane compound represented by Chemical Formula 2, and a tetraalkylammonium hydroxide having 2 to 5 carbon atoms at a temperature of 5° C. or below, the production of by-products having a high molecular weight can be minimized, and high purity polyhedral oligomeric silsesquioxanes can be synthesized with a high yield.

If the reaction temperature exceeds 5° C., the yield of random or ladder-type polysilsesquioxane having a high molecular weight increases and the purity of the polyhedral oligomeric silsesquioxanes is lowered, and as the base catalyst, if a base catalyst other than tetraalkylammonium hydroxide having 2 to 5 carbon atoms is used, the yield of the polyhedral oligomeric silsesquioxanes may decrease.

The reaction temperature may be controlled to about −5° C. to 5° C., about −3° C. to 5° C., about 0° C. to 5° C., about −3° C. to 3° C., about 0° C. to 3° C. or about 0° C. to effectively provide high purity polyhedral oligomeric silsesquioxanes.

The first silane compound used in the preparation method of one embodiment is a precursor for introducing a hydrocarbon group substituted with a halogen into the polyhedral oligomeric silsesquioxanes.

In particular, as the first silane compound, a compound in which $R^1$ is a monovalent moiety derived from a hydrocarbon substituted with fluorine may be used to impart properties such as low refractive index, water repellency, oil repellency, chemical resistance, skid resistance, wear resistance, etc., to the polyhedral oligomeric silsesquioxanes.

Specifically, as the first silane compound, a compound in which $R^1$ is trifluoromethyl, trifluoroethyl, trifluoropropyl, trifluorobutyl, pentafluorobutyl, trifluoropentyl, pentafluoropentyl, heptafluoropentyl, trifluorohexyl, pentafluorohexyl, heptafluorohexyl, nonafluorohexyl, trifluoroheptyl, pentafluoroheptyl, heptafluoroheptyl, nonafluoroheptyl, dodecafluoroheptyl, chloropropyl, (chloromethyl)phenyl, (chloromethyl)phenylethyl, or dibromoethyl can be used.

Further, in the first silane compound, three of $X^1$ may be the same or different, and may be various leaving groups as defined above.

More specifically, as the first silane compound, at least one selected from the group consisting of (trifluoropropyl)trimethoxysilane, (trifluorobutyl)trimethoxysilane, (pentafluorobutyl)trimethoxysilane, (trifluoropentyl)trimethoxysilane, (pentafluoropentyl)trimethoxysilane, (heptafluoropentyl)trimethoxysilane, (trifluorohexyl)trimethoxysilane, (pentafluorohexyl)trimethoxysilane, (heptafluorohexyl)trimethoxysilane, (nonafluorohexyl)trimethoxysilane, (trifluoroheptyl)trimethoxysilane, (pentafluoroheptyl)trimethoxysilane, (heptafluoroheptyl)trimethoxysilane, (nonafluoroheptyl)trimethoxysilane, (dodecafluoroheptyl)trimethoxysilane, (chloropropyl)trimethoxysilane, [(chloromethyl)phenyl]trimethoxysilane, [(chloromethyl)phenylethyl]trimethoxysilane, (dibromoethyl)trimethoxysilane, and the like may be used.

The second silane compound used in the preparation method of one embodiment is a precursor for introducing a reactive functional group to the polyhedral oligomeric silsesquioxanes.

These reactive functional groups may not only impart scratch resistance or the like by increasing the hardness of a coating layer containing the polyhedral oligomeric silsesquioxanes, but may also improve adhesion to a substrate of the coating layer.

$R^2$, which is a reactive functional group in Chemical Formula 2, may be a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —NH$_2$, —NH—R$^6$, —NH$_3$X$^3$, —COON, —CONH$_2$, —CN, —SH, a glycidyl group, a glycidyloxy group, and maleimide.

As used herein, the epoxyalkyl group having 2 to 30 carbon atoms may be a linear, branched, or cyclic alkyl group.

Specifically, the epoxyalkyl group having 2 to 30 carbon atoms may be an epoxycyclohexyl group or the like.

The epoxyalkoxy group having 2 to 30 carbon atoms refers to a functional group in which the epoxyalkyl group having 2 to 30 carbon atoms is linked to A or Si in Chemical Formula 2 via —O—.

Examples of the epoxyalkoxy group having 2 to 30 carbon atoms include an epoxycycloheptoxy group and the like.

The alkenyl group having 2 to 30 carbon atoms refers to a monovalent moiety derived from a linear, branched, or cyclic alkene having 2 to 30 carbon atoms.

Specifically, examples of the alkenyl group having 2 to 30 carbon atoms include a vinyl group, allyl group, a norbornene group, and the like.

The alkenyloxy group having 2 to 30 carbon atoms refers to a functional group in which the alkenyl group having 2 to 30 carbon atoms is linked to A or Si in Chemical Formula 2 via —O—.

Examples of the alkenyloxy group having 2 to 30 carbon atoms include a vinyloxy group, an allyloxy group, and the like.

Specific examples of the hydrocarbons substituted with at least one substituent selected from the group consisting of —OH, —NH$_2$, —NH—R$^6$, —NH$_3$X$^3$, —COON, —CONH$_2$, —CN, —SH, a glycidyl group, a glycidyloxy group, and maleimide may be as described below, but are not limited thereto.

The hydrocarbons having 1 to 30 carbon atoms substituted with a hydroxy group (—OH) may be those in which at least one hydrogen in a linear, branched, or cyclic hydrocarbon having 1 to 30 carbon atoms is substituted with a hydroxyl group.

Specific examples of the hydrocarbons having 1 to 30 carbon atoms substituted with the hydroxy group (—OH) include cyclohexanediol, trimethylolpropane, glycerol, 3-hydroxy-3-methylbutane, and the like.

The hydrocarbons having 1 to 30 carbon atoms substituted with an amino group (—NH$_2$) may be those in which at least one hydrogen in a linear, branched, or cyclic hydrocarbon having 1 to 30 carbon atoms is substituted with an amino group.

Specific examples of the hydrocarbons having 1 to 30 carbon atoms substituted with the amino group (—NH$_2$) include aminopropane, aniline (aminobenzene), and the like.

The hydrocarbons having 1 to 30 carbon atoms substituted with an amino group (—NH—R$^6$) may be those in which at least one hydrogen in a linear, branched, or cyclic hydrocarbon having 1 to 30 carbon atoms is substituted with —NH—R$^6$.

Accordingly, the carbon number of the hydrocarbons substituted with —NH—R$^6$ may exceed 30, and the upper limit of the total number of carbon atoms may be adjusted to 60 or less according to the upper limit of the number of carbon atoms of R$^6$. Specific examples of the hydrocarbons having 1 to 30 carbon atoms substituted with —NH—R$^6$ include N-methylaminopropane, N-phenylaminopropane, N-(aminoethyl)aminopropane, and the like The hydrocarbons having 1 to 30 carbon atoms substituted with an ammonium group (—NH$_3$X$^3$) may be those in which at least one hydrogen in a linear, branched, or cyclic hydrocarbon having 1 to 30 carbon atoms is substituted with an ammonium group.

Specific examples of the hydrocarbons having 1 to 30 carbon atoms substituted with the ammonium group include propylammonium chloride and the like.

The hydrocarbons having 1 to 30 carbon atoms substituted with a cyano group (—CN) may be those in which at least one hydrogen in a linear, branched, or cyclic hydrocarbon having 1 to 30 carbon atoms is substituted with a cyano group.

Specific examples of the hydrocarbons having 1 to 30 carbon atoms substituted with the cyano group include propylnitrile and the like.

The hydrocarbons having 1 to 30 carbon atoms substituted with a mercapto group (—SH) may be those in which at least one hydrogen in a linear, branched, or cyclic hydrocarbon having 1 to 30 carbon atoms is substituted with a mercapto group.

Specific examples of the hydrocarbons having 1 to 30 carbon atoms substituted with the mercapto group include propylthiol and the like.

The hydrocarbons having 1 to 30 carbon atoms substituted with a glycidyloxy group may be those in which at least one hydrogen in a linear, branched, or cyclic hydrocarbon having 1 to 30 carbon atoms is substituted with a glycidyloxy group.

Specific examples of the hydrocarbons having 1 to 30 carbon atoms substituted with the glycidyloxy group include glycidyloxypropane and the like.

The hydrocarbons having 1 to 30 carbon atoms substituted with maleimide may be those in which at least one hydrogen in a linear, branched, or cyclic hydrocarbon having 1 to 30 carbon atoms is substituted with maleimide.

Specific examples of hydrocarbons having 1 to 30 carbon atoms substituted with maleimide include N-propylmaleimide and the like.

Further, specific examples of the hydrocarbons having 1 to 30 carbon atoms substituted with at least two substituents selected from the group consisting of —OH, —NH$_2$, —NH—R$^6$, —NH$_3$X$^3$, —COOH, —CONH$_2$, —CN, —SH, a glycidyl group, a glycidyloxy group, and maleimide include maleamic acid in which two hydrogen atoms of ethene are substituted with COOH and —CONH$_2$, respectively, among the substituents, and the like.

The R$^2$ in Chemical Formula 2 may be a monovalent radical in which one hydrogen radical is removed from the substituted hydrocarbons described above.

The R$^2$ in Chemical Formula 2 may be linked directly to Si, or may be linked to Si via A.

In the former case, A may be a single bond. In the latter case, A may be various bivalent organic groups defined above.

Specifically, A may be a single bond, methylene, ethylene, propylene, phenylene, —O—Si(CH$_3$)(CH$_3$)—, —O—Si(CH$_3$)(CH$_3$)—CH$_2$CH$_2$CH$_2$—, etc.

Similarly to the case of the first silane compound, three of X$^2$ in the second silane compound may be the same or different, and may be various leaving groups as defined above.

More specifically, as the second silane compound, at least one selected from the group consisting of (3-(meth)acryloxypropyl)trimethoxysilane, (2,3-dihydroxypropoxypropyl)trimethoxysilane, (3,4-dihydroxyhexylethyl)trimethoxysilane, (3-hydroxy-3-methylbutyldimethylsiloxy)trimethoxysilane 3,4-epoxyhexylpropyl)trimethoxysilane, (3,4-epoxyhexylethyldimethylsiloxy)trimethoxysilane, (3-aminopropyl)trimethoxysilane, (N-aminoethylaminopropyl)trimethoxysilane, (aminophenyl)trimethoxysilane, (N-phenylaminopropyl)trimethoxysilane, (N-methylaminopropyl)trimethoxysilane, (3-cyanopropyl)trimethoxysilane, (3-mercaptopropyl)trimethoxysilane, (3-glycidyloxypropyl)trimethoxysilane, vinyltrimethoxysilane, allyltrimethoxysilane, (trimethoxysilyl)norbornene, N-[3-(trimethoxysilyl)propyl]maleimide, N-[3-(trimethoxysilyl)propyl]maleamic acid, and the like may be used.

The polyhedral oligomeric silsesquioxanes prepared by the preparation method according to one embodiment may be represented by Chemical Formula 3 below.

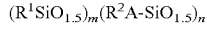    [Chemical Formula 3]

In Chemical Formula 3, R$^1$ and R$^2$ are the same as those defined in Chemical Formulae 1 and 2, and m and n are each independently an integer of 1 to 13, with the proviso that the sum of m and n is an integer of 6 to 14.

The m and n in Chemical Formula 3 may be controlled depending on the mole ratio used for the first silane compound and the second silane compound.

Accordingly, the use amount of the first silane compound and the second silane compound can be controlled depending on the structure of the polyhedral oligomeric silsesquioxanes to be prepared.

In one example, in the case of preparing a polyhedral oligomeric silsesquioxane with the formula of $(R^1SiO_{1.5})_4$ $(R^2\text{-}A\text{-}SiO_{1.5})_4$, the first silane compound and the second silane compound may be used in a molar ratio of about 4:4.

In the preparation method according to one embodiment, the first silane compound and the second silane compound are reacted in the presence of a base catalyst.

In particular, the yield of the product can be further increased by using a tetraalkylammonium hydroxide having 2 to 5 carbon atoms as a base catalyst.

As the tetraalkylammonium hydroxide having 2 to 5 carbon atoms, a tetraalkylammonium hydroxide in which four alkyl groups linked to N are each independently an alkyl group having 2 to 5 carbon atoms can be used.

Specifically, as the tetraalkylammonium hydroxide having 2 to 5 carbon atoms, tetraethylammonium hydroxide, tetrapropylammonium hydroxide, tetrabutylammonium hydroxide, tetrapentylammonium hydroxide, or a mixture thereof may be used.

Among these, when tetrabutylammonium hydroxide is used as the base catalyst, it is possible to minimize side reactions and further improve the synthesis yield of the polyhedral oligomeric silsesquioxanes.

The tetraalkylammonium hydroxide having 2 to 5 carbon atoms may be used in an amount of 0.001 to 100 moles, 0.001 to 50 moles, 0.001 to 10 moles, 0.001 to 5 moles, or 1 to 5 moles based on 100 moles of the entire silane compounds.

Within such a range, it is possible to minimize side reactions and synthesize high purity polyhedral oligomeric silsesquioxanes with a high yield.

Further, in the preparation method according to one embodiment, the reaction mixture can be reacted in the presence of an organic solvent.

Accordingly, it is possible to further inhibit the production of by-products having high molecular weights of other structures, in addition to the polyhedral oligomeric silsesquioxanes having a cage structure.

As the organic solvent, an organic solvent capable of exhibiting appropriate solubility for the first and second silane compounds without affecting the reaction of the first and second silane compounds may be used without limitation.

In one example, as the organic solvent, an ether solvent, such as diethyl ether or tetrahydrofuran, may be used.

The reaction mixture containing the first and second silane compounds may be reacted at a low temperature within the above-mentioned range for an appropriate time.

Although the reaction time is not particularly limited, the yield of the polyhedral oligomeric silsesquioxanes can be increased by reacting for about 5 to 128 hours.

The polyhedral oligomeric silsesquioxanes prepared by the method described above may have high purity and may exhibit low refractive index properties.

In one example, the polyhedral oligomeric silsesquioxanes may have a refractive index of about 1.20 to 1.50 as measured with an Abbe refractometer.

The polyhedral oligomeric silsesquioxanes exhibiting a low refractive index as described above can be used in a low refractive index layer of an antireflection film of a display device, thereby implementing very low reflectivity.

In particular, when the polyhedral oligomeric silsesquioxanes are used, a conventional high-temperature process of producing bubbles and thus realizing a low refractive index can be eliminated, and thus it is expected to economically provide a high-quality antireflection film.

Hereinafter, the action and effects of the present invention will be described in detail by way of specific examples.

However, these examples are given for illustrative purposes only, and the scope of the invention is not intended to be limited by these examples.

Example 1: Synthesis of Polyhedral Oligomeric Silsesquioxane 25 g (114.55 mmol) of (3,3,3-trifluoropropyl)trimethoxysilane and 8.9 g (37.98 mmol) of (3-acryloxypropyl)trimethoxysilane were dissolved in 150 mL of THF (tetrahydrofuran), and 26.2 g (number of moles of $N(Bu)_4OH$: 5.05 mmol) of a 5 wt % tetrabutylammonium hydroxide aqueous solution was added thereto. Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 22.9 g of liquid polyhedral oligomeric silsesquioxane (TA62) (yield: 97.9%).

The refractive index of TA62 was 1.411 as measured with an Abbe refractometer (DTM-1, manufactured by ATAGO).

$^1$H NMR (400 MHz): 6.392 (2H, br), 6.122 (2H, br), 5.826 (2H, br), 4.129 (4H, br), 2.120 (12H, br), 1.735 (4H, br), 0.904 (12H, br), 0.724 (4H, br)

Example 2: Synthesis of Polyhedral Oligomeric Silsesquioxane 20 g (91.64 mmol) of (3,3,3-trifluoropropyl)trimethoxysilane and 21.5 g (91.75 mmol) of (3-acryloxypropyl)trimethoxysilane were dissolved in 180 mL of THF (tetrahydrofuran), and 31.4 g (number of moles of $N(Bu)_4OH$: 6.05 mmol) of a 5 wt % tetrabutylammonium hydroxide aqueous solution was added thereto.

Then, the reaction mixture was stirred at 0° C. for 72 hours.

After completion of the reaction, the reaction product was dried under reduced pressure and then dissolved in 200 mL of ethyl acetate, and by-products were extracted four times with a NaCl aqueous solution.

Then, the organic layer was dried over $MgSO_4$ and filtered, and the filtrate was dried under reduced pressure to obtain 27.2 g of liquid polyhedral oligomeric silsesquioxane (TA44) (yield: 94.1%).

The refractive index of TA44 was 1.435 as measured with an Abbe refractometer (DTM-1, manufactured by ATAGO).

$^1$H NMR (400 MHz): 6.392 (4H, br), 6.122 (4H, br), 5.826 (4H, br), 4.129 (8H, br), 2.120 (8H, br), 1.735 (8H, br), 0.904 (8H, br), 0.724 (8H, br)

Example 3: Synthesis of Polyhedral Oligomeric Silsesquioxane 7.8 g (35.74 mmol) of (3,3,3-trifluoropropyl)trimethoxysilane and 25.1 g (107.12 mmol) of (3-acryloxypropyl)trimethoxysilane were dissolved in 140 mL of THF (tetrahydrofuran), and 24.5 g (number of moles of $N(Bu)_4OH$: 4.72 mmol) of a 5 wt % tetrabutylammonium hydroxide aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 21.4 g of liquid polyhedral oligomeric silsesquioxane (TA26) (yield: 93.0%).

The refractive index of TA26 was 1.453 as measured with an Abbe refractometer (DTM-1, manufactured by ATAGO).

$^1$H NMR (400 MHz): 6.392 (6H, br), 6.122 (6H, br), 5.826 (6H, br), 4.129 (12H, br), 2.120 (4H, br), 1.735 (12H, br), 0.904 (4H, br), 0.724 (12H, br)

Example 4: Synthesis of Polyhedral Oligomeric Silsesquioxane 25 g (67.88 mmol) of (nonafluorohexyl)trimethoxysilane and 5.3 g (22.62 mmol) of (3-acryloxypropyl)trimethoxysilane were dissolved in 90 mL of THF (tetrahydrofuran), and 15.5 g (number of moles of $N(Bu)_4OH$: 2.99 mmol) of a 5 wt % tetrabutylammonium hydroxide aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 23 g of liquid polyhedral oligomeric silsesquioxane (NA62) (yield: 95.6%).

The refractive index of NA62 was 1.373 as measured with an Abbe refractometer (DTM-1, manufactured by ATAGO).

$^1$H NMR (400 MHz): 6.379 (2H, br), 6.108 (2H, br), 5.805 (2H, br), 4.118 (4H, br), 2.118 (12H, br), 1.753 (4H, br), 0.918 (12H, br), 0.705 (4H, br)

Example 5: Synthesis of Polyhedral Oligomeric Silsesquioxane 20 g (54.31 mmol) of (nonafluorohexyl)trimethoxysilane and 12.7 g (54.20 mmol) of (3-acryloxypropyl)trimethoxysilane were dissolved in 110 mL of THF (tetrahydrofuran), and 18.6 g (number of moles of $N(Bu)_4OH$: 3.58 mmol) of a 5 wt % tetrabutylammonium hydroxide aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 24.2 g of liquid polyhedral oligomeric silsesquioxane (NA44) (yield: 96.0%).

The refractive index of NA44 was 1.404 as measured with an Abbe refractometer (DTM-1, manufactured by ATAGO).

$^1$H NMR (400 MHz): 6.379 (4H, br), 6.108 (4H, br), 5.805 (4H, br), 4.118 (8H, br), 2.118 (8H, br), 1.753 (8H, br), 0.918 (8H, br), 0.705 (8H, br)

Example 6: Synthesis of Polyhedral Oligomeric Silsesquioxane 10 g (27.15 mmol) of (nonafluorohexyl)trimethoxysilane and 19.1 g (81.51 mmol) of (3-acryloxypropyl)trimethoxysilane were dissolved in 110 mL of THF (tetrahydrofuran), and 18.6 g (number of moles of $N(Bu)_4OH$: 3.58 mmol) of a 5 wt % tetrabutylammonium hydroxide aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 20.5 g of liquid polyhedral oligomeric silsesquioxane (NA26) (yield: 94.9%).

The refractive index of NA26 was 1.433 as measured with an Abbe refractometer (DTM-1, manufactured by ATAGO).

$^1$H NMR (400 MHz): 6.379 (6H, br), 6.108 (6H, br), 5.805 (6H, br), 4.118 (12H, br), 2.118 (4H, br), 1.753 (12H, br), 0.918 (4H, br), 0.705 (12H, br)

Comparative Example 1: Synthesis of Polyhedral Oligomeric Silsesquioxane 25 g (114.55 mmol) of (3,3,3-trifluoropropyl)trimethoxysilane and 8.9 g (37.98 mmol) of (3-acryloxypropyl)trimethoxysilane were dissolved in 150 mL of THF (tetrahydrofuran), and 9.2 g (number of moles of $N(CH_3)_4OH$: 5.05 mmol) of a 5 wt % $N(CH_3)_4OH$ aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over $MgSO_4$ and filtered, and the filtrate was dried under reduced pressure to obtain 21 g of liquid polyhedral oligomeric silsesquioxane (TA62) (yield: 89.7%).

The refractive index of TA62 was 1.411 as measured with an Abbe refractometer (DTM-1, manufactured by ATAGO).

$^1$H NMR (400 MHz): 6.392 (2H, br), 6.122 (2H, br), 5.826 (2H, br), 4.129 (4H, br), 2.120 (12H, br), 1.735 (4H, br), 0.904 (12H, br), 0.724 (4H, br)

Comparative Example 2: Synthesis of Polyhedral Oligomeric Silsesquioxane 20 g (91.64 mmol) of (3,3,3-trifluoropropyl)trimethoxysilane and 21.5 g (91.75 mmol) of (3-acryloxypropyl)trimethoxysilane were dissolved in 180 mL of THF (tetrahydrofuran), and 11 g (number of moles of $N(CH_3)_4OH$: 6.03 mmol) of a 5 wt % $N(CH_3)_4OH$ aqueous solution was added thereto. Then, the reaction mixture was stirred at 0° C. for 72 hours.

After completion of the reaction, the reaction product was dried under reduced pressure and then dissolved in 200 mL of ethyl acetate, and by-products were extracted four times with a NaCl aqueous solution.

Then, the organic layer was dried over $MgSO_4$ and filtered, and the filtrate was dried under reduced pressure to obtain 23.5 g of liquid polyhedral oligomeric silsesquioxane (TA44) (yield: 81.3%).

The refractive index of TA44 was 1.435 as measured with an Abbe refractometer (DTM-1, manufactured by ATAGO).

$^1$H NMR (400 MHz): 6.392 (4H, br), 6.122 (4H, br), 5.826 (4H, br), 4.129 (8H, br), 2.120 (8H, br), 1.735 (8H, br), 0.904 (8H, br), 0.724 (8H, br)

Comparative Example 3: Synthesis of Polyhedral Oligomeric Silsesquioxane 7.8 g (35.74 mmol) of (3,3,3-trifluoropropyl)trimethoxysilane and 25.1 g (107.12 mmol) of (3-acryloxypropyl)trimethoxysilane were dissolved in 140 mL of THF (tetrahydrofuran), and 8.6 g (number of moles of N(CH$_3$)$_4$OH: 4.72 mmol) of a 5 wt % N(CH$_3$)$_4$OH aqueous solution was added thereto.

Then, the reaction mixture was stirred at 0° C. for 72 hours.

After completion of the reaction, the reaction product was dried under reduced pressure and then dissolved in 150 mL of ethyl acetate, and by-products were extracted four times with a NaCl aqueous solution.

Then, the organic layer was dried over MgSO$_4$ and filtered, and the filtrate was dried under reduced pressure to obtain 19.5 g of liquid polyhedral oligomeric silsesquioxane (TA26) (yield: 84.7%).

The refractive index of TA26 was 1.453 as measured with an Abbe refractometer (DTM-1, manufactured by ATAGO).

$^1$H NMR (400 MHz): 6.392 (6H, br), 6.122 (6H, br), 5.826 (6H, br), 4.129 (12H, br), 2.120 (4H, br), 1.735 (12H, br), 0.904 (4H, br), 0.724 (12H, br)

Comparative Example 4: Synthesis of Polyhedral Oligomeric Silsesquioxane 25 g (114.55 mmol) of (3,3,3-trifluoropropyl)trimethoxysilane and 8.9 g (37.98 mmol) of (3-acryloxypropyl)trimethoxysilane were dissolved in 150 mL of THF (tetrahydrofuran), and 9.2 g (number of moles of N(CH$_3$)$_4$OH: 5.05 mmol) of a 5 wt % N(CH$_3$)$_4$OH aqueous solution was added thereto.

Then, the reaction mixture was stirred at room temperature (about 25° C.) for 72 hours.

After completion of the reaction, the reaction product was dried under reduced pressure and then dissolved in 150 mL of ethyl acetate, and by-products were extracted four times with a NaCl aqueous solution.

Then, the organic layer was dried over MgSO$_4$ and filtered, and the filtrate was dried under reduced pressure to obtain 20 g of liquid polyhedral oligomeric silsesquioxane (TA62) (yield: 85.5%).

The refractive index of TA62 was 1.411 as measured with an Abbe refractometer (DTM-1, manufactured by ATAGO).

$^1$H NMR (400 MHz): 6.392 (2H, br), 6.122 (2H, br), 5.826 (2H, br), 4.129 (4H, br), 2.120 (12H, br), 1.735 (4H, br), 0.904 (12H, br), 0.724 (4H, br)

Comparative Example 5: Synthesis of Polyhedral Oligomeric Silsesquioxane 20 g (91.64 mmol) of (3,3,3-trifluoropropyl)trimethoxysilane and 21.5 g (91.75 mmol) of (3-acryloxypropyl)trimethoxysilane were dissolved in 180 mL of THF (tetrahydrofuran), and 11 g (number of moles of N(CH$_3$)$_4$OH: 6.03 mmol) of a 5 wt % N(CH$_3$)$_4$OH aqueous solution was added thereto.

Then, the reaction mixture was stirred at room temperature for 72 hours.

After completion of the reaction, the reaction product was dried under reduced pressure and then dissolved in 200 mL of ethyl acetate, and by-products were extracted four times with a NaCl aqueous solution.

Then, the organic layer was dried over MgSO$_4$ and filtered, and the filtrate was dried under reduced pressure to obtain 23 g of liquid polyhedral oligomeric silsesquioxane (TA44) (yield: 79.6%).

The refractive index of TA44 was 1.435 as measured with an Abbe refractometer (DTM-1, manufactured by ATAGO).

$^1$H NMR (400 MHz): 6.392 (4H, br), 6.122 (4H, br), 5.826 (4H, br), 4.129 (8H, br), 2.120 (8H, br), 1.735 (8H, br), 0.904 (8H, br), 0.724 (8H, br)

Comparative Example 6: Synthesis of Polyhedral Oligomeric Silsesquioxane 7.8 g (35.74 mmol) of (3,3,3-trifluoropropyl)trimethoxysilane and 25.1 g (107.12 mmol) of (3-acryloxypropyl)trimethoxysilane were dissolved in 140 mL of THF (tetrahydrofuran), and 8.6 g (number of moles of N(CH$_3$)$_4$OH: 4.72 mmol) of a 5 wt % N(CH$_3$)$_4$OH aqueous solution was added thereto.

Then, the reaction mixture was stirred at room temperature for 72 hours.

After completion of the reaction, the reaction product was dried under reduced pressure and then dissolved in 150 mL of ethyl acetate, and by-products were extracted four times with a NaCl aqueous solution.

Then, the organic layer was dried over MgSO$_4$ and filtered, and the filtrate was dried under reduced pressure to obtain 19 g of liquid polyhedral oligomeric silsesquioxane (TA26) (yield: 82.6%).

The refractive index of TA26 was 1.453 as measured with an Abbe refractometer (DTM-1, manufactured by ATAGO).

$^1$H NMR (400 MHz): 6.392 (6H, br), 6.122 (6H, br), 5.826 (6H, br), 4.129 (12H, br), 2.120 (4H, br), 1.735 (12H, br), 0.904 (4H, br), 0.724 (12H, br)

Experimental Example: Evaluation of Purity of Polyhedral Oligomeric Silsesquioxanes The purity of the polyhedral oligomeric silsesquioxanes prepared in Examples 1 to 6 and Comparative Examples 1 to 6 was determined by area % using GPC (Gel Permeation Chromatography). At this time, polystyrene was used as a standard sample, THF was used as a solvent, and an ELS (Evaporative Light Scattering) detector was used as a detector.

The yield and purity of the polyhedral oligomeric silsesquioxanes prepared in the examples and comparative examples are shown in Table 1 below.

TABLE 1

|  | Yield [%] | Purity [Area %] |
|---|---|---|
| Example 1 | 97.9 | 93 |
| Example 2 | 94.1 | 87 |
| Example 3 | 93.0 | 75 |
| Example 4 | 95.6 | 90 |
| Example 5 | 96.0 | 88 |
| Example 6 | 94.9 | 79 |
| Comparative Example 1 | 89.7 | 93 |
| Comparative Example 2 | 81.3 | 86 |
| Comparative Example 3 | 84.7 | 71 |
| Comparative Example 4 | 85.5 | 81 |

TABLE 1-continued

| | Yield [%] | Purity [Area %] |
|---|---|---|
| Comparative Example 5 | 79.6 | 58 |
| Comparative Example 6 | 82.6 | 58 |

Referring to Table 1 above, according to one embodiment of the present invention, it was confirmed that high purity polyhedral oligomeric silsesquioxanes could be provided with a high yield.

In contrast, Comparative Examples 1 to 6 employed tetramethylammonium hydroxide as a base catalyst, thus providing polyhedral oligomeric silsesquioxanes with a low yield. In particular, Comparative Examples 4 to 6 provided low purity polyhedral oligomeric silsesquioxanes with a low yield as the synthesis temperature was adjusted to room temperature.

The invention claimed is:

1. A method for preparing a polyhedral oligomer silsesquioxane comprising the step of: reacting a reaction mixture containing a first silane compound represented by Chemical Formula 1 below, a second silane compound represented by Chemical Formula 2 below, and a tetraalkylammonium hydroxide having 2 to 5 carbon atoms at a temperature of 5° C. or below:

$$R^1\text{—}SiX^1{}_3 \qquad \text{[Chemical Formula 1]}$$

$$R^2\text{-A-}SiX^2{}_3 \qquad \text{[Chemical Formula 2]}$$

wherein, in Chemical Formulae 1 and 2, A is a single bond, an alkylene group having 1 to 10 carbon atoms, an arylene group having 6 to 30 carbon atoms, —O—Si($R^3$)($R^4$)—, or —O—Si($R^3$)($R^4$)—$R^5$—, $R^1$ is a monovalent moiety derived from a hydrocarbon having 1 to 30 carbon atoms substituted with a halogen, $R^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —$NH_2$, —NH—$R^6$, —$NH_3X^3$, —COON, —$CONH_2$, —CN, —SH, a glycidyl group, a glycidyloxy group, and maleimide, $X^1$ and $X^2$ are each independently an alkoxy group having 1 to 5 carbon atoms, Cl, Br, or I, $R^3$ and $R^4$ are each independently an alkyl group having 1 to 5 carbon atoms, $R^5$ is an alkylene group having 1 to 12 carbon atoms, $R^6$ is an alkyl group having 1 to 10 carbon atoms, an aryl group having 6 to 30 carbon atoms, or an alkyl group having 1 to 10 carbon atoms substituted with an amino group, and $X^3$ is a halogen.

2. The method for preparing a polyhedral oligomer silsesquioxane of claim 1, wherein, as the first silane compound, a compound in which $R^1$ is trifluoromethyl, trifluoroethyl, trifluoropropyl, trifluorobutyl, pentafluorobutyl, trifluoropentyl, pentafluoropentyl, heptafluoropentyl, trifluorohexyl, pentafluorohexyl, heptafluorohexyl, nonafluorohexyl, trifluoroheptyl, pentafluoroheptyl, heptafluoroheptyl, nonafluoroheptyl, dodecafluoroheptyl, chloropropyl, (chloromethyl)phenyl, (chloromethyl)phenylethyl, or dibromoethyl is used.

3. The method for preparing a polyhedral oligomer silsesquioxane of claim 1, wherein, as the second silane compound, a compound in which $R^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxycyclohexyl group, an epoxycycloheptoxy group, a vinyl group, an allyl group, and a norbornene group, or a monovalent moiety derived from a hydrocarbon substituted with at least one substituent selected from the group consisting of cyclohexanediol, trimethylolpropane, glycerol, 3-hydroxy-3-methylbutane, aminopropyl, aniline, N-methylaminopropane, N-phenylaminopropane, N-(aminoethyl)aminopropane, propylammonium chloride, propylnitrile, propylthiol, glycidyloxypropane, N-propylmaleimide, and maleamic acid is used.

4. The method for preparing a polyhedral oligomer silsesquioxane of claim 1, wherein, as the second silane compound, a compound in which A is a single bond, methylene, ethylene, propylene, phenylene, —O—Si($CH_3$)($CH_3$)—, or —O—Si($CH_3$)($CH_3$)—$CH_2CH_2CH_2$— is used.

5. The method for preparing a polyhedral oligomer silsesquioxane of claim 1, wherein, as first silane compound, at least one selected from the group consisting of (trifluoropropyl)trimethoxysilane, (trifluorobutyl)trimethoxysilane, (pentafluorobutyl)trimethoxysilane, (trifluoropentyl)trimethoxysilane, (pentafluoropentyl)trimethoxysilane, (heptafluoropentyl)trimethoxysilane, (trifluorohexyl)trimethoxysilane, (pentafluorohexyl)trimethoxysilane, (heptafluorohexyl)trimethoxysilane, (nonafluorohexyl)trimethoxysilane, (trifluoroheptyl)trimethoxysilane, (pentafluoroheptyl)trimethoxysilane, (heptafluoroheptyl)trimethoxysilane, (nonafluoroheptyl)trimethoxysilane, (dodecafluoroheptyl)trimethoxysilane, (chloropropyl)trimethoxysilane, [(chloromethyl)phenyl]trimethoxysilane, [(chloromethyl)phenylethyl]trimethoxysilane, (dibromoethyl)trimethoxysilane, and the like is used.

6. The method for preparing a polyhedral oligomer silsesquioxane of claim 1, wherein, as the second silane compound, at least one selected from the group consisting of (3-(meth)acryloxypropyl)trimethoxysilane, (2,3-dihydroxypropoxypropyl)trimethoxysilane, (3,4-dihydroxyhexylethyl)trimethoxysilane, (3-hydroxy-3-methylbutyldimethylsiloxy)trimethoxysilane (3,4-epoxyhexylpropyl)trimethoxysilane, (3,4-epoxyhexylethyldimethylsiloxy)trimethoxysilane, (3-aminopropyl)trimethoxysilane, (N-aminoethylaminopropyl)trimethoxysilane, (aminophenyl)trimethoxysilane, (N-phenylaminopropyl)trimethoxysilane, (N-methylaminopropyl)trimethoxysilane, (3-cyanopropyl)trimethoxysilane, (3-mercaptopropyl)trimethoxysilane, (3-glycidyloxypropyl)trimethoxysilane, vinyltrimethoxysilane, allyltrimethoxysilane, (trimethoxysilyl)norbornene, N-[3-(trimethoxysilyl)propyl]maleimide, N-[3-(trimethoxysilyl)propyl]maleamic acid, and the like is used.

7. The method for preparing a polyhedral oligomer silsesquioxane of claim 1, wherein, as the tetraalkylammonium hydroxide having 2 to 5 carbon atoms, tetrabutylammonium hydroxide is used.

8. The method for preparing a polyhedral oligomer silsesquioxane of claim 1, wherein the tetraalkylammonium hydroxide having 2 to 5 carbon atoms is used in an amount of 0.001 to 100 moles based on 100 moles of the entire silane compound.

9. The method for preparing a polyhedral oligomer silsesquioxane of claim 1, wherein the reaction mixture is reacted in the presence of an organic solvent.

10. The method for preparing a polyhedral oligomer silsesquioxane of claim 9, wherein, as the organic solvent, an ether solvent is used.

11. The method for preparing a polyhedral oligomer silsesquioxane of claim 1, wherein the reaction mixture is reacted for 5 to 128 hours.

12. The method for preparing a polyhedral oligomer silsesquioxane of claim 1, wherein the polyhedral oligomer silsesquioxane is represented by Chemical Formula 3 below:

     [Chemical Formula 3]

wherein, in Chemical Formula 3, A is a single bond, an alkylene group having 1 to 10 carbon atoms, an arylene group having 6 to 30 carbon atoms, —O—Si($R^3$)($R^4$)—, or —O—Si($R^3$)($R^4$)—$R^5$—, $R^1$ is a monovalent moiety derived from a hydrocarbon having 1 to 30 carbon atoms substituted with a halogen, $R^2$ is a functional group selected from the group consisting of a (meth)acryloyl group, a (meth)acryloyloxy group, a hydroxy group, a mercapto group, a carboxyl group, an amino group, a cyano group, a glycidyl group, a glycidyloxy group, an epoxyalkyl group having 2 to 30 carbon atoms, an epoxyalkoxy group having 2 to 30 carbon atoms, an alkenyl group having 2 to 30 carbon atoms, and an alkenyloxy group having 2 to 30 carbon atoms, or a monovalent moiety derived from a hydrocarbon having 1 to 30 carbon atoms substituted with at least one substituent selected from the group consisting of —OH, —$NH_2$, —NH—$R^6$, —$NH_3X^3$, —COOH, —$CONH_2$, —CN, —SH, a glycidyl group, a glycidyloxy group, and maleimide, $R^3$ and $R^4$ are each independently an alkyl group having 1 to 5 carbon atoms, $R^5$ is an alkylene group having 1 to 12 carbon atoms, $R^6$ is an alkyl group having 1 to 10 carbon atoms, an aryl group having 6 to 30 carbon atoms, or an alkyl group having 1 to 10 carbon atoms substituted with an amino group, $X^3$ is a halogen, and m and n are each independently an integer of 1 to 13, with the proviso that the sum of m and n is an integer of 6 to 14.

* * * * *